(12) United States Patent
Song et al.

(10) Patent No.: US 7,935,538 B2
(45) Date of Patent: May 3, 2011

(54) INDICATOR IMMOBILIZATION ON ASSAY DEVICES

(75) Inventors: Xuedong Song, Roswell, GA (US); Curtis Sayre, Atlanta, GA (US); Shawn R. Feaster, Duluth, GA (US); Julie Villanueva, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 178 days.

(21) Appl. No.: 11/640,100

(22) Filed: Dec. 15, 2006

(65) Prior Publication Data
US 2008/0145949 A1   Jun. 19, 2008

(51) Int. Cl.
*G01N 33/53* (2006.01)

(52) U.S. Cl. ............ 436/514; 436/528; 436/810; 435/4; 435/287.1; 435/288.7; 435/970; 422/50; 422/55; 422/56; 422/68.1

(58) Field of Classification Search .......... 422/50, 422/55, 56, 68.1; 435/4, 287.1, 288.7; 436/518, 436/528
See application file for complete search history.

(56) References Cited

U.S. PATENT DOCUMENTS

| | | | |
|---|---|---|---|
| 3,951,748 A | 4/1976 | Devlin |
| 4,483,920 A | 11/1984 | Gillespie et al. |
| 4,637,979 A | 1/1987 | Skjold et al. |
| 4,657,855 A | 4/1987 | Corey et al. |
| 4,742,011 A | 5/1988 | Blake et al. |
| 4,743,560 A | 5/1988 | Campbell et al. |
| 4,748,116 A | 5/1988 | Simonsson et al. |
| 4,806,311 A | 2/1989 | Greenquist |
| 4,806,423 A | 2/1989 | Hugl et al. |
| 4,814,271 A | 3/1989 | Hugl et al. |
| 4,828,985 A | 5/1989 | Self |
| 4,835,099 A | 5/1989 | Mize et al. |
| 4,889,816 A | 12/1989 | Davis et al. |
| 4,895,809 A | 1/1990 | Schlabach et al. |
| 4,904,583 A | 2/1990 | Mapes et al. |
| 4,920,045 A | 4/1990 | Okuda |
| 4,943,522 A | 7/1990 | Eisinger et al. |
| 4,954,435 A | 9/1990 | Krauth |
| 4,956,302 A | 9/1990 | Gordon et al. |
| 4,978,625 A | 12/1990 | Wagner et al. |
| 4,980,298 A | 12/1990 | Blake et al. |
| 5,003,178 A | 3/1991 | Livesay |

(Continued)

FOREIGN PATENT DOCUMENTS

DE     4403437 A1     8/1995

(Continued)

OTHER PUBLICATIONS

Japanese Abstract JP2001021563 Specific Bonding Body, Jan. 26, 2001.

(Continued)

*Primary Examiner* — Bao-Thuy L Nguyen
(74) *Attorney, Agent, or Firm* — Dority & Manning, P.A.

(57) ABSTRACT

A lateral flow assay device for detecting the presence or quantity of an analyte in a test sample is provided. The device comprises a chromatographic medium that defines a detection zone, wherein a crosslinked network is non-diffusively immobilized within the detection zone. The crosslinked network contains a small molecule indicator that is configured to undergo a detectable color change in the presence of the analyte.

15 Claims, 1 Drawing Sheet

U.S. PATENT DOCUMENTS

| | | | |
|---|---|---|---|
| 5,073,340 A | 12/1991 | Covington et al. | |
| 5,075,078 A | 12/1991 | Osikowicz et al. | |
| 5,120,643 A | 6/1992 | Ching et al. | |
| 5,149,622 A | 9/1992 | Brown et al. | |
| 5,178,831 A * | 1/1993 | Sakota et al. | 422/56 |
| 5,185,127 A | 2/1993 | Vonk | |
| 5,208,143 A | 5/1993 | Henderson et al. | |
| 5,238,652 A | 8/1993 | Sun et al. | |
| 5,252,459 A | 10/1993 | Tarcha et al. | |
| 5,252,743 A | 10/1993 | Barrett et al. | |
| 5,275,785 A | 1/1994 | May et al. | |
| 5,354,692 A | 10/1994 | Yang et al. | |
| 5,395,754 A | 3/1995 | Lambotte et al. | |
| 5,409,664 A | 4/1995 | Allen | |
| 5,428,690 A | 6/1995 | Bacus et al. | |
| 5,434,054 A | 7/1995 | Pollmann et al. | |
| 5,464,739 A | 11/1995 | Johnson et al. | |
| 5,547,833 A | 8/1996 | Dorval et al. | |
| 5,559,041 A | 9/1996 | Kang et al. | |
| 5,569,608 A | 10/1996 | Sommer | |
| 5,571,667 A | 11/1996 | Chu et al. | |
| 5,571,684 A | 11/1996 | Lawrence et al. | |
| 5,573,919 A | 11/1996 | Kearns et al. | |
| 5,591,645 A | 1/1997 | Rosenstein | |
| 5,602,040 A | 2/1997 | May et al. | |
| 5,604,110 A | 2/1997 | Baker et al. | |
| 5,608,006 A * | 3/1997 | Myerson | 525/54.1 |
| 5,610,077 A | 3/1997 | Davis et al. | |
| 5,622,871 A | 4/1997 | May et al. | |
| 5,656,503 A | 8/1997 | May et al. | |
| 5,658,747 A | 8/1997 | Feldsine et al. | |
| 5,663,044 A | 9/1997 | Noffsinger et al. | |
| 5,670,381 A | 9/1997 | Jou et al. | |
| 5,686,315 A | 11/1997 | Pronovost et al. | |
| 5,712,172 A | 1/1998 | Huang et al. | |
| 5,714,389 A | 2/1998 | Charlton et al. | |
| 5,741,662 A | 4/1998 | Madsen et al. | |
| 5,750,359 A | 5/1998 | Huh et al. | |
| 5,786,137 A | 7/1998 | Diamond et al. | |
| 5,788,863 A | 8/1998 | Milunic | |
| 5,798,273 A | 8/1998 | Shuler et al. | |
| 5,807,752 A | 9/1998 | Brizgys et al. | |
| 5,874,216 A | 2/1999 | Mapes | |
| 5,939,331 A | 8/1999 | Burd et al. | |
| 5,945,281 A | 8/1999 | Prabhu | |
| 5,962,995 A | 10/1999 | Avnery | |
| 5,989,921 A | 11/1999 | Charlton et al. | |
| 5,989,924 A | 11/1999 | Root et al. | |
| 5,989,926 A | 11/1999 | Bradley et al. | |
| 5,998,221 A | 12/1999 | Malick et al. | |
| 6,057,165 A | 5/2000 | Mansour | |
| 6,077,669 A | 6/2000 | Little et al. | |
| 6,130,100 A | 10/2000 | Jobling et al. | |
| 6,133,048 A | 10/2000 | Penfold et al. | |
| 6,140,136 A | 10/2000 | Lee | |
| 6,156,271 A | 12/2000 | May | |
| 6,187,269 B1 | 2/2001 | Lancesseur et al. | |
| 6,194,220 B1 | 2/2001 | Malick et al. | |
| 6,197,537 B1 | 3/2001 | Rao et al. | |
| 6,235,464 B1 | 5/2001 | Henderson et al. | |
| 6,274,324 B1 | 8/2001 | Davis et al. | |
| 6,294,391 B1 | 9/2001 | Bradley et al. | |
| 6,348,319 B1 | 2/2002 | Braach-Maksvytis et al. | |
| 6,352,862 B1 | 3/2002 | Davis et al. | |
| 6,376,195 B1 | 4/2002 | Mapes | |
| 6,399,398 B1 | 6/2002 | Cunningham et al. | |
| 6,407,492 B1 | 6/2002 | Avnery et al. | |
| 6,436,651 B1 | 8/2002 | Everhart et al. | |
| 6,485,926 B2 | 11/2002 | Nemori et al. | |
| 6,486,227 B2 | 11/2002 | Nohr et al. | |
| 6,515,194 B2 | 2/2003 | Neading et al. | |
| 6,524,864 B2 | 2/2003 | Fernandez de Castro | |
| 6,541,277 B1 | 4/2003 | Kang et al. | |
| 6,607,922 B2 | 8/2003 | LaBorde | |
| 6,627,459 B1 | 9/2003 | Tung et al. | |
| 6,653,149 B1 | 11/2003 | Tung et al. | |
| 6,669,908 B2 | 12/2003 | Weyker et al. | |
| RE38,430 E | 2/2004 | Rosenstein | |
| 6,699,722 B2 | 3/2004 | Bauer et al. | |
| 6,737,277 B1 | 5/2004 | Kang et al. | |
| 6,767,710 B2 | 7/2004 | DiNello et al. | |
| 6,780,896 B2 | 8/2004 | MacDonald et al. | |
| 6,875,185 B2 | 4/2005 | Wong et al. | |
| 6,905,835 B2 | 6/2005 | Sorell Gomez et al. | |
| 6,951,631 B1 | 10/2005 | Catt et al. | |
| 6,979,576 B1 | 12/2005 | Cheng et al. | |
| 6,998,246 B2 | 2/2006 | Schaffler et al. | |
| 7,026,002 B1 | 4/2006 | Goerlach-Graw et al. | |
| 7,044,919 B1 | 5/2006 | Catt et al. | |
| 7,049,150 B2 | 5/2006 | Bachand | |
| 7,052,831 B2 | 5/2006 | Fletcher et al. | |
| 2002/0042149 A1 | 4/2002 | Butlin et al. | |
| 2002/0045273 A1 | 4/2002 | Butlin et al. | |
| 2002/0173047 A1 * | 11/2002 | Hudak et al. | 436/178 |
| 2003/0119204 A1 | 6/2003 | Wei et al. | |
| 2003/0124739 A1 | 7/2003 | Song et al. | |
| 2004/0043507 A1 | 3/2004 | Song et al. | |
| 2004/0043511 A1 | 3/2004 | Song et al. | |
| 2004/0043512 A1 | 3/2004 | Song et al. | |
| 2004/0121334 A1 | 6/2004 | Wei et al. | |
| 2004/0121480 A1 | 6/2004 | Wei et al. | |
| 2004/0151632 A1 | 8/2004 | Bradley et al. | |
| 2004/0161859 A1 | 8/2004 | Guo et al. | |
| 2004/0197819 A1 | 10/2004 | Yang et al. | |
| 2004/0197820 A1 | 10/2004 | Wei et al. | |
| 2005/0029924 A1 | 2/2005 | Okay et al. | |
| 2005/0036148 A1 | 2/2005 | Phelan et al. | |
| 2005/0037510 A1 | 2/2005 | Sharrock et al. | |
| 2005/0109951 A1 | 5/2005 | Fish et al. | |
| 2005/0112635 A1 | 5/2005 | Gentle et al. | |
| 2005/0112779 A1 | 5/2005 | Wei et al. | |
| 2005/0112780 A1 | 5/2005 | Song | |
| 2005/0131287 A1 * | 6/2005 | Kaylor et al. | 600/362 |
| 2005/0191704 A1 | 9/2005 | Boga et al. | |
| 2005/0250169 A1 * | 11/2005 | Gonzalez et al. | 435/18 |
| 2006/0029976 A1 | 2/2006 | McVicker et al. | |
| 2006/0127924 A1 | 6/2006 | Hellyer et al. | |
| 2006/0166374 A1 | 7/2006 | Hubscher | |
| 2006/0223189 A1 * | 10/2006 | Kawanishi et al. | 436/90 |
| 2006/0223193 A1 | 10/2006 | Song et al. | |
| 2006/0228711 A1 | 10/2006 | Yamamoto | |
| 2006/0240569 A1 | 10/2006 | Goldenbaum et al. | |
| 2006/0246601 A1 | 11/2006 | Song et al. | |
| 2007/0019502 A1 | 1/2007 | Foley et al. | |
| 2007/0048182 A1 | 3/2007 | Song et al. | |
| 2007/0048815 A1 | 3/2007 | Song | |
| 2008/0050839 A1 * | 2/2008 | Suslick et al. | 436/164 |

FOREIGN PATENT DOCUMENTS

| | | |
|---|---|---|
| EP | 19940582231 A1 | 2/1994 |
| EP | 19960696735 A1 | 2/1996 |
| EP | 19970806666 A2 | 11/1997 |
| EP | 1034758 A1 | 9/2000 |
| EP | 20040893690 B1 | 7/2004 |
| GB | 2183160 A | 6/1987 |
| WO | WO 8602736 | 5/1986 |
| WO | WO 9401775 | 2/1994 |
| WO | WO 9627614 | 9/1996 |
| WO | WO 9738312 | 10/1997 |
| WO | WO 9964863 | 12/1999 |
| WO | WO 0031538 | 6/2000 |
| WO | WO 0031539 | 6/2000 |
| WO | WO 0186302 A1 | 11/2001 |
| WO | WO 03025115 | 3/2003 |
| WO | WO 03052379 | 6/2003 |
| WO | WO 03056293 | 7/2003 |
| WO | WO 03058246 A1 | 7/2003 |
| WO | WO 03089902 | 10/2003 |
| WO | WO 2004068105 | 8/2004 |
| WO | WO 2004092341 | 10/2004 |
| WO | WO 2005003732 | 1/2005 |
| WO | WO 2005021753 | 3/2005 |
| WO | WO 2005057215 | 6/2005 |
| WO | WO 2005059547 | 6/2005 |
| WO | WO 2005086744 A2 | 9/2005 |
| WO | WO 2005086744 A3 | 9/2005 |
| WO | WO 2005095967 | 10/2005 |

| | | |
|---|---|---|
| WO | WO 2006062626 | 6/2006 |
| WO | WO 2006118622 A1 | 11/2006 |
| WO | WO 2007027353 A2 | 3/2007 |
| WO | WO 2007027353 A3 | 3/2007 |

OTHER PUBLICATIONS

Japanese Abstract JP2003057240 Immunoassay Method, Feb. 26, 2003.

Japanese Abstract JP2003210193 Method and Apparatus for Detecting Presence of Microbe and Determining Physiological Status Thereof, Jul. 29, 2003.

Japanese Abstract JP2005300401 Membrane Immobilization Method of Protein, Oct. 27, 2005.

Japanese Abstract JP7270412 Small Molecule Measurement, Oct. 20, 1995.

Xuedong Song, U.S. Appl. No. 11/217,112, filed Aug. 31, 2005, Diagnostic Test Kits with Improved Detection Accuracy.

Xuedong Song, U.S. Appl. No. 11/589,671, filed Oct. 30, 2006, Absorbent Article Containing Lateral Flow Assay Device.

Sayre et al., U.S. Appl. No. 11/513,898, filed Aug. 30, 2006, Detection of Hydrogen Peroxide Released by Enzyme-Catalyzed Oxidation of an Analyte.

Rameshbabu Boga et al., U.S. Appl. No. 11/638,760, filed Dec. 14, 2006, Detection of Formaldehyde In Urine Samples.

Xuedong Song, U.S. Appl. No. 11/640,116, filed Dec. 15, 2006, Lateral Flow Assay Device and Absorbent Article Containing Same.

Kaylor et al., U.S. Appl. No. 11/012,759, filed Dec. 15, 2004, Sample-Efficient Lateral Flow Immunoassay.

Search Report and Written Opinion for PCT/IB2007/053962 dated Apr. 28, 2008.

* cited by examiner

INDICATOR IMMOBILIZATION ON ASSAY DEVICES

BACKGROUND

Various analytical procedures and devices are commonly employed to determine the presence and/or concentration of analytes that may be present in a test sample. In some cases, the mere presence of an analyte may, for example, indicate the existence of tissue or organ damage. Likewise, abnormal concentrations of an analyte may indicate infection, such as a bacterial or viral infection. One conventional technique for detecting the presence of an enzymatic analyte is described in U.S. Pat. No. 6,348,319 to Braach-Maksvytis, et al. Braach-Maksvytis, et al. functions by sensing the digestion of a substrate by the enzyme. For example, FIG. 1 of Braach-Maksvytis. et al. illustrates a device 10 that includes a first zone 11 and a second zone 12. The first zone 11 is provided with polymer beads 13 (carrier) linked to streptavidin 14 (reporter) via a peptide linker 15 that is cleavable by a protease 16. Upon addition of the protease 16, the streptavidin 14 is released and passes to the second zone 12, which includes a biosensor membrane 17 that detects the presence of streptavidin through a change in the impedance of the membrane. (Col. 5, II. 25-30). Unfortunately, however, techniques such as described by Braach-Maksvytis, et al., are far too complex and cost prohibitive for certain types of applications, such as those requiring a relatively quick diagnosis by a patient (self-diagnosis or with the aid of medical personnel).

As a result, assays have been developed that are more 'user friendly'. For instance, assays have been developed that utilize indicators susceptible to a visible or detectable change upon action of an analyte. If the indicator undergoes a detectable change, e.g., a color change, the user may be confident that the analyte is present in the test sample. For example, U.S. Pat. No. 5,409,664 to Allen describes an assay device including an amine-functionalized bibulous assay strip including a signal producing system. Specifically, the reagent strip is impregnated with one or more members of the detectable signal reagent system. For example, when determining the amount of cholesterol in a sample, one could have cholesterol esterase in a first zone, cholesterol oxidase in a second zone, and horseradish peroxidase in a third zone.

Despite such improvements, assays still present numerous difficulties. For instance, small molecular indicators usually work well in wet chemistry applications, in which a test sample is combined with a reagent-containing solution, but they are not equally suitable for use in dry chemistry applications due to, for instance, inability to maintain the dry small molecule indicators in an active state and at a specific location on a device during shipping and handling prior to use. However, such dry chemistry applications are preferred due to there relative simplicity, speed of detection, and low cost.

As such, a need currently exists for improved assay devices, in particular for assay devices directed to dry chemistry applications.

SUMMARY

In accordance with one embodiment, a lateral flow assay device is disclosed for detecting the presence or quantity of an analyte in a test sample. The device comprises a chromatographic medium that defines a detection zone, wherein a crosslinked network is non-diffusively immobilized within the detection zone. The crosslinked network contains a small molecule indicator that is configured to undergo a detectable color change in the presence of the analyte.

BRIEF DESCRIPTION OF THE DRAWINGS

A full and enabling disclosure, including the best mode, directed to one of ordinary skill in the art, is set forth more particularly in the remainder of the specification, which makes reference to the appended FIGURE in which.

DETAILED DESCRIPTION OF REPRESENTATIVE EMBODIMENTS

Definitions

Figure 1:
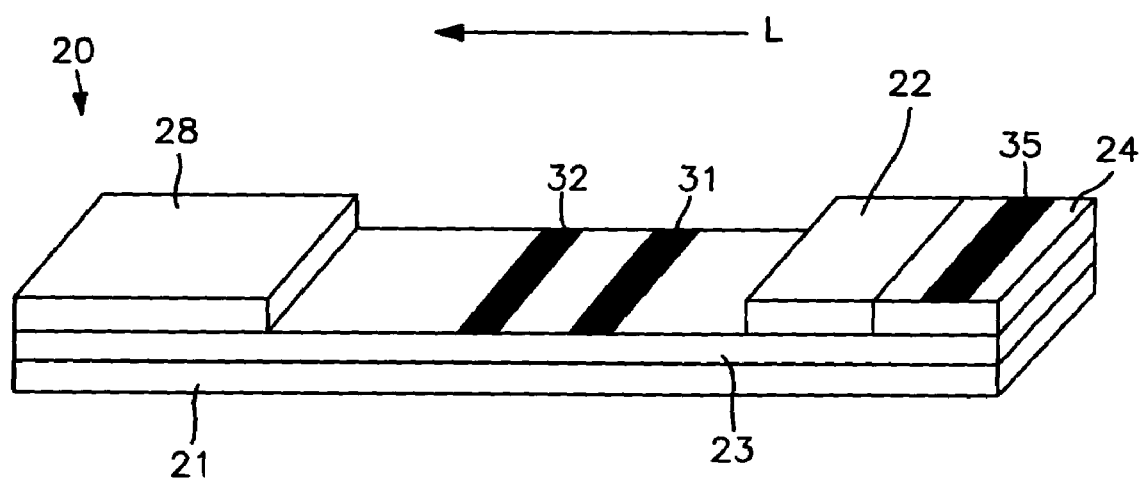
FIG. 1 is a perspective view of one embodiment of a flow-through assay device as described herein.

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; C-reactive protein; lipocalins; IgE antibodies; vitamin B2 micro-globulin; glycated hemoglobin (Gly. Hb); cortisol; digitoxin; bilirubin; urobilinogen; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; maynabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "test sample" generally refers to a material suspected of containing the analyte. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The test sample may be pretreated prior to use, such as preparing plasma from blood, diluting viscous fluids, and the like. Methods of treatment may involve filtration, precipitation, dilution, distillation, mixing, concentration, inactivation of interfering components, and the addition of reagents. Besides physiological fluids, other liquid samples may be used such as water, food products and the like for the performance of environmental or food production assays. In addition, a solid material suspected of containing the analyte may be used as the test sample. In some instances it may be beneficial to modify a solid test sample to form a liquid medium or to release the analyte.

Detailed Description

Reference will now be made in detail to various embodiments of the disclosed subject matter, one or more examples of which are set forth below. Each example is provided by way of explanation, not limitation of the subject matter. In fact, it will be apparent to those skilled in the art that various modifications and variations may be made without departing from the scope or spirit of the disclosure. For instance, features illustrated or described as part of one embodiment, may be used on another embodiment to yield a still further embodiment. Thus, it is intended that the present disclosure covers such modifications and variations as come within the scope of the appended claims and their equivalents.

Generally speaking, the present invention is directed to a method of securely immobilizing small molecule indicators onto a chromatographic medium of a lateral flow assay device. The indicator is a reactive chemical moiety that reacts with an analyte or with a reaction product that is generated through a process that requires participation of the analyte. Upon reaction with the analyte (or reaction product thereof), the indicator may exhibit a detectable color change. The indicator is typically a moiety of a small molecule in that the size of a small molecule is generally less than about 3000 Daltons (i.e., atomic mass units, one Dalton being equivalent to $\frac{1}{12}$ the mass of a $^{12}C$ isotope) prior to any derivitizations, e.g., addition of reactive functionalities to the small molecule indicator. In other embodiments, the small molecule indicator may be less than about 2000 Daltons, in some embodiments less than about 1000 Daltons, and in some embodiments, less than about 500 Daltons. As used herein, the term 'indicator' may refer to either the reactive moiety capable of generating a detection signal upon reaction with an analyte or reaction product thereof or alternatively may refer to the small molecule that includes the indicator moiety.

Various types of small molecule indicators may be employed in the present invention. In one embodiment, for example, diazonium ion indicators are employed for the detection of various analytes, such as bilirubin and urobilinogen. For instance, the analyte may directly couple a diazonium ion to produce a product that differs in color from the starting materials. Diazonium ions may also be utilized in indirect detection of analytes, such as glucose and various proteins. That is, the analyte may initially react with a reagent, such as protein or an enzymatic substrate, to form a reaction product that in turn reacts with the diazonium ion to yield a detectable product. The diazonium ion may have the following generic formula:

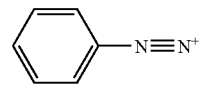

The diazonium ion may be zwitterionic in that the counterion of the diazonium moiety is covalently bound to the ring system. The ring system of the diazonium ion may be substituted or unsubstituted.

When considering the detection of an analyte with a diazonium indicator, the analyte or a reaction product thereof is capable of undergoing electrophilic attack by the diazonium ion. This reaction is often referred to as "coupling" and results in the formation of a product having a color different from that of the starting indicator reagent. For example, diazonium ions may react with aromatic compounds to form an aromatic azo compound having the generic formula, R—N=N—R', wherein "R" and "R'" are aryl groups. Without intending to be limited by theory, it is believed that this reaction induces either a shift of the absorption maxima towards the red end of the spectrum ("bathochromic shift") or towards the blue end of the spectrum ("hypsochromic shift"). The type of absorption shift depends on the nature of the resulting azo molecule and whether it functions as an electron acceptor (oxidizing agent), in which a hypsochromic shift results, or whether it functions as an electron donor (reducing agent), in which a bathochromic shift results. The absorption shift provides a color difference that is detectable, either visually or through instrumentation, to indicate the presence of the analyte within the test sample. For example, prior to contact with an infected test sample, the diazonium ion may be colorless or it may possess a certain color. However, after contacting the test sample and reacting with the analyte, or a reaction product formed in a process that requires participation of the analyte, an aromatic azo compound will form that exhibits a color that is different than the initial color of the diazonium ion.

Diazonium ions may also be utilized to directly or indirectly detect the presence of an enzyme. For instance, an enzymatic substrate may be provided for detection of an enzyme (e.g., hydrolytic enzyme, such as leukocyte esterase). The provided substrate may be chemically acted upon (e.g., cleaved in the case of a protease) by the enzyme of interest to form a product. When detecting leukocyte esterase, for example, the substrate may be an aromatic ester that is catalytically hydrolyzed in the presence of leukocyte esterase to yield an aromatic compound. The aromatic esters may include, for instance, indoxyl esters having the following general formula:

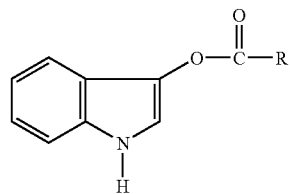

wherein, R may be substituted or unsubstituted, and may be an alkyl group, an alkyoxy group, a hydroxyalkyl group, an alkylene group, a fatty acid group, and so forth. In addition, the aromatic rings may also be substituted or unsubstituted. Specific examples include, for instance, indoxyl acetate, indoxyl butyrate, indoxyl laureate, indoxyl stearate, indoxyl ester of a N-blocked amino acid or peptide and thioindoxyl analogs thereof, and N-Tosyl-L-alanine 3-indoxyl ester. Such indoxyl esters are hydrolyzed by the leukocyte esterase to form a benzopyrrole, such as indoxyl, which has the following structure:

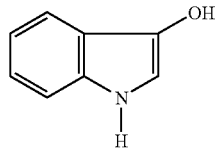

Lactate esters may also be used as substrates for enzyme detection. For example, lactate esters may be used such as described in U.S. Pat. No. 5,464,739 to Johnson. et al. and U.S. Pat. No. 5,663,044 to Noffsinger, et al., which are incorporated herein in their entirety by reference thereto for all purposes. Lactate esters are generally hydrolyzed by leukocyte esterase to provide a hydroxy-pyrrole compound. Other suitable ester substrates include thiazole esters, pyrrole esters, thiophene esters, naphthyl esters, phenoxyl esters, quinolinyl esters, such as described in U.S. Pat. No. 5,750, 359 to Huh, et al.; U.S. Pat. No. 4,657,855 to Corey, et al.; and Japanese Publication No. 03210193 to Kawanishi, et al., which are incorporated herein in their entirety by reference thereto for all purposes.

Still other suitable substrates for hydrolytic enzymes include, for instance, amides, peptides, ethers, or other chemical compounds having an enzymatically-hydrolyzable bond. Specific types of substrates may include proteins or glycoproteins, peptides, nucleic acids (e.g., DNA and RNA), carbohydrates, lipids, esters, derivatives thereof, and so forth. For instance, some suitable substrates for peptidases and/or proteases may include peptides, proteins, and/or glycoproteins, such as casein (e.g., β-casein, azocasein, etc.), albumin (e.g., bovine serum albumin), hemoglobin, myoglobin, keratin, gelatin, insulin, proteoglymay, fibronectin, laminin, collagen, elastin, and so forth. Still other suitable substrates are described in U.S. Pat. No. 4,748,116 to Simonsson, et al.; U.S. Pat. No. 5,786,137 to Diamond, et al.; U.S. Pat. No. 6,197,537 to Rao, et al.; and U.S. Pat. No. 6,235,464 to Henderson, et al.; U.S. Pat. No. 6,485,926 to Nemori. et al., which are incorporated herein in their entirety by reference thereto for all purposes.

Regardless of the manner in which the reaction is conducted, an aromatic compound may be formed through reaction of the analyte with the substrate that is capable of inducing a color change in the presence of a diazonium ion via a coupling reaction. Specific examples of diazonium salts that may be used include, without limitation, diazonium chlorides, diazonium acid sulphates, diazonium alkyl sulphates, diazonium fluoborates, diazonium benzenesulphonates, diazonium acid 1,5-naphthalenedisulphonates, and so forth. Specific examples of diazonium salts are 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl)benzene diazonium chloride; 4-diazo-3-hydroxy-7-bromo-1-naphthylsulfonate; and 4-diazo-3-hydroxy-7-[1,oxopropyl]-1-naphthylsulfonate. One particularly desired diazonium salt is 5-chloro-2-methoxybenzenediazonium chloride, which has a yellow color and is classified under the name "Diazo Red RC" or "Fast Red RC." More specifically, "Fast Red RC" has the following structure:

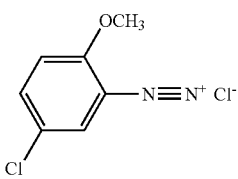

Other suitable diazonium salts are classified by the common names "Fast Red B" and "Fast Blue B." Still other suitable diazonium salts may be described in U.S. Pat. No. 4,637,979 to Skjold, et al.; U.S. Pat. No. 4,806,423 to Hugh, et al.; and U.S. Pat. No. 4,814,271 to Hugl, et al., which are incorporated herein in their entirety by reference thereto for all purposes.

Diazonium salts may also be utilized in a direct detection technique in which the diazonium ion directly binds to a particular analyte. For example, in one embodiment, the disclosed devices may be utilized in detection of analytes such as bilirubin and/or urobilinogen. Increased levels of bilirubin as well as the reduction products of bilirubin, e.g., urobilinogen, may be an indicator of several disease states including, for instance, malaria, sickle cell anemia, hepatitis B, hepatitis C, hepatotoxicity, alcoholism, cirrhosis, Gilbert's syndrome, gallstones, and maycers including pancreatic maycer, ductal carcinoma as well as metastatic carcinomas in general. A non-limiting listing of diazonium compounds suitable for use in the direct detection of bilirubin may include p-aminobenzenesulfonic acid, 2,6-dichlorobenzene diazonium tetrafluoroborate, 2-trifluoromethylbenzene diazonium, and so on.

Diazonium ions that preferentially couple urobilinogen may include those having the following general structure

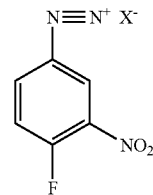

In which X⁻ represents a stabilizing anion.

In another embodiment, a diazonium ion having the following general structure may be used for the preferential detection of urobilinogen:

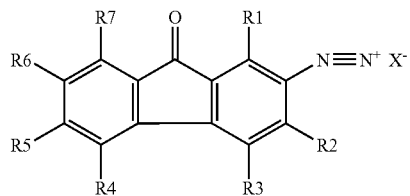

wherein R1 through R7 are independently a hydrogen atom, a halogen atom, a lower alkyl group or a lower alkoxy group; and X is a stabilizing anion. A non-limiting listing of diazonium compounds that may be utilized to preferentially directly couple urobilinogen may include 4-fluoro-3-nitrobenzenediazonium salt, 4-methoxybenzene-diazonium-tetrafluoroborate, 3,3'-dimethoxybiphenyl-4,4'-diazonium salt, and the like.

The present disclosure is not limited to diazonium-type small molecule indicators. Many other small molecule indicators are generally known to one of ordinary skill in the art and are encompassed in the present disclosure. For example, Erhlich reagents are small molecule indicators that may be used in the detection of urobilinogen in a test sample. Erhlich reagents are p-aminobenzaldehyde molecules that may preferentially bind urobilinogen. Erhlich reagents for detection of urobilinogen may include, without limitation, dialkylaminobenzaldehydes such as dimethylaminobenzaldehyde and diethylaminobenzaldehyde.

Another exemplary class of small molecule indicators that may be anchored to a chromatographic medium according to the present disclosure may include the benzidine-type indicators. Benzidine-type indicators may undergo changes of color in the presence of peroxides, and thus are often utilized in detection of peroxidatively active substances such as, for example, glucose, occult blood, electrolytes, cholesterol, and a variety of proteins as are generally known in the art. Benzidine-type indicators have the following general structure:

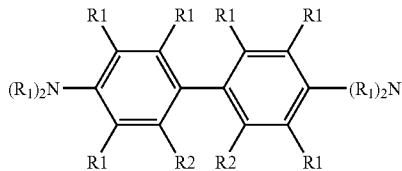

in which the R1 and R2 substituents may be independently selected from hydrogen, lower alkyl (i.e., alkyl having 1 to about 6 carbon atoms), lower alkyloxy (i.e., alkyloxy having 1 to about 6 carbon atoms), aryl or aryloxy. R1 and R2 may be independently substituted such as with hydroxy, halogen, cyano, and so on. Moreover, the R2 substituents may together form $(CH_2)_n$ in which n is 1 or 2. Typical compounds embraced by the term "benzidine-type" indicator include benzidine, o-tolidine, o-dianisidine, 3,3',5,5'-tetramethylbenzidine (tetramethylbenzidine (TMB)), 3,3',5,5'-tetra(alkyl) benzidine, the various N- and N'-substituted benzidines and others.

Another exemplary class of small molecule indicators encompassed by the present disclosure is the phthaleins. Phthaleins such as phenolphthalein (Hln), dibromothymol-sulfonephthalein (bromothymol blue, BTB), octabromophenol-sulfophthalein (tetrabromophenol blue), octachlorophenol-sulfophthalein (tetrachlorophenol blue), as well as the mixed halogenated analogues, for example, 3',3'',5',5''-tetrabromophenol-3,4,5,6-tetrachlorosulfophthalein 3',3'',5',5''-tetrachlorophenol-3,4,5,6-tetrabromosulfophthalein and 3',3''-dichloro-5',5''-dibromophenol-3,4,5,6-tetrachlorosulfophthalein, are small molecule indicators that may be utilized, for example, in determination of pH, which may in turn indicate the presence of an analyte in a test sample such as, for example, the presence of protein.

In accordance with the present invention, a crosslinked network containing the indicator is formed on a chromatographic medium of a lateral flow device. Without intending to be limited by theory, it is believed that the crosslinked network may help durably secure the indicator, thereby allowing a user to more readily detect a change in its color during use. The crosslinked network may contain "intra-cross links" (i.e., covalent bonds between functional groups of a single molecule) and/or "inter-cross links" (i.e., covalent bonds between different molecules, e.g., between two indicator molecules or between an indicator molecule and the substrate surface).

Crosslinking may be carried out via self crosslinking of the indicator and/or through the inclusion of a separate crosslinking agent. Suitable crosslinking agents, for instance, may include polyglycidyl ethers, such as ethylene glycol diglycidyl ether and polyethylene glycol dicglycidyl ether; acrylamides; compounds containing one or more hydrolyzable groups, such as alkoxy groups (e.g., methoxy, ethoxy and propoxy); alkoxyalkoxy groups (e.g., methoxyethoxy, ethoxyethoxy and methoxypropoxy); acyloxy groups (e.g., acetoxy and octanoyloxy); ketoxime groups (e.g., dimethylketoxime, methylketoxime and methylethylketoxime); alkenyloxy groups (e.g., vinyloxy, isopropenyloxy, and 1-ethyl-2-methylvinyloxy); amino groups (e.g., dimethylamino, diethylamino and butylamino); aminoxy groups (e.g., dimethylaminoxy and diethylaminoxy); and amide groups (e.g., N-methylacetamide and N-ethylacetamide).

Any of a variety of different crosslinking mechanisms may be employed in the present invention, such as thermal initiation (e.g., condensation reactions, addition reactions, etc.), electromagnetic radiation, and so forth. Some suitable examples of electromagnetic radiation that may be used in the present invention include, but are not limited to, electron beam radiation, natural and artificial radio isotopes (e.g., α, β, and γ rays), x-rays, neutron beams, positively-charged beams, laser beams, ultraviolet, etc. Electron beam radiation, for instance, involves the production of accelerated electrons by an electron beam device. Electron beam devices are generally well known in the art. For instance, in one embodiment, an electron beam device may be used that is available from Energy Sciences, Inc., of Woburn, Mass. under the name "Microbeam LV." Other examples of suitable electron beam devices are described in U.S. Pat. No. 5,003,178 to Livesay; U.S. Pat. No. 5,962,995 to Avnery; U.S. Pat. No. 6,407,492 to Avnery, et al., which are incorporated herein in their entirety by reference thereto for all purposes. The wavelength λ of the radiation may vary for different types of radiation of the electromagnetic radiation spectrum, such as from about $10^{-14}$ meters to about $10^{-5}$ meters. Electron beam radiation, for instance, has a wavelength λ of from about $10^{-13}$ meters to about $10^{-9}$ meters. Besides selecting the particular wavelength λ of the electromagnetic radiation, other parameters may also be selected to control the degree of crosslinking. For example, the dosage may range from about 0.1 megarads (Mrads) to about 10 Mrads, and in some embodiments, from about 1 Mrads to about 5 Mrads.

The source of electromagnetic radiation may be any radiation source known to those of ordinary skill in the art. For example, an excimer lamp or a mercury lamp with a D-bulb may be used. Other specialty-doped lamps that emit radiation at a fairly narrow emission peak may be used with photoinitiators which have an equivalent absorption maximum. For example, the V-bulb, available from Fusion Systems, is another suitable lamp for use. In addition, specialty lamps having a specific emission band may be manufactured for use with one or more specific photoinitiators.

Initiators may be employed in some embodiments that enhance the functionality of the selected crosslinking technique. Thermal initiators, for instance, may be employed in certain embodiments, such as azo, peroxide, persulfate, and redox initiators. Representative examples of suitable thermal initiators include azo initiators such as 2,2'-azobis(2,4-dimethylvaleronitrile), 2,2'-azobis(isobutyronitrile), 2,2'-azobis-2-methylbutyronitrile, 1,1'-azobis(1-cyclohexanecarbonitrile), 2,2'-azobis(methyl isobutyrate), 2,2'-azobis(2.-amidinopropane)dihydrochloride, and 2,2'-azobis(4-methoxy-2,4-dimethylvaleronitrile); peroxide initiators such as benzoyl peroxide, acetyl peroxide, lauroyl peroxide, decanoyl peroxide, dicetyl peroxydicarbonate, di(4-t-butylcyclohexyl)peroxydicarbonate, di(2-ethylhexyl)peroxydicarbonate, t-butylperoxypivalate, t-butylperoxy-2-ethylhexanoate, and dicumyl peroxide; persulfate initiators such as potassium persulfate, sodium persulfate, and ammonium persulfate; redox (oxidation-reduction) initiators such as combinations of the above persulfate initiators with reducing agents such as sodium metabisulfite and sodium bisulfite, systems based on organic peroxides and tertiary amines, and systems based on organic hydroperoxides and transition metals; other initiators such as pinacols; and the like (and mixtures thereof). Azo compounds and peroxides are generally preferred. Photoinitiators may likewise be employed, such as substituted acetophenones, such as benzyl dimethyl ketal and 1-hydroxycyclohexyl phenyl ketone; substituted alpha-ketols, such as 2-methyl-2-hydroxypropiophenone; benzoin ethers, such as benzoin methyl ether and benzoin isopropyl ether; substituted benzoin ethers, such as anisoin methyl ether; aromatic sulfonyl chlorides; photoactive oximes; and so forth (and mixtures thereof). Other suitable photoinitiators may be described in U.S. Pat. No. 6,486,227 to Nohr, et al. and U.S. Pat. No. 6,780,896 to MacDonald, et al., both of which are incorporated herein by reference.

Although not required, additional components may also be employed within the crosslinked network to facilitate the securement of the indicator. For example, an anchoring compound may be employed that links the indicator to the surface of the chromatographic medium and further improves the durability of the indicator on the lateral flow device. Typically, the anchoring compound is larger in size than the indicator, which improves its likelihood of remaining on the surface of the chromatographic medium during use. For example, the anchoring compound may include a macromolecular compound, such as a polymer, oligomer, dendrimer, particle, etc. Polymeric anchoring compounds may be natural, synthetic, or combinations thereof. Examples of natural polymeric anchoring compounds include, for instance, polypeptides, proteins, DNA/RNA and polysaccharides (e.g., glucose-based polymers). Examples of synthetic polymeric anchoring compounds include, for instance, polyacrylic acid and polyvinyl alcohols. One particular example of a polysaccharide anchoring compound is activated dextran. In some embodiments, the anchoring compound may be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles are utilized. Although any synthetic particle may be used, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles may generally vary. In one particular embodiment, for instance, the particles are spherical in shape. However, it should be understood that other shapes are also contemplated such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns.

The manner in which the anchoring compound is used to link the indicator and the chromatographic medium may vary. In one embodiment, for instance, the anchoring compound is attached to the indicator prior to application of both to the chromatographic medium. In other embodiments, the anchoring compound may be bonded to the chromatographic medium prior to application of the indicator. In still other embodiments, the materials may be applied as separate components to the chromatographic medium and attachment reactions can take place in situ, optionally at the same time as the crosslinking of the network. For instance, the small molecule indicator may bind the anchoring compound, the anchoring compound may bind the medium, and simultaneously, cross-linking reactions can take place between anchoring compounds, between indicators, or between the two. In one such embodiment, the cross-linked network thus formed may be physically held on the porous membrane of the chromatographic medium without the need for bonding between the porous membrane and the other components of the system. In particular, the crosslinked network, portions of which may extend within and among the pores of the porous membrane, may be physically constrained on the membrane, even without specific bonds forming between the membrane and the components of the crosslinked network.

In the case of bonds being formed between the system components, attachment of the anchoring compound to a chromatographic medium as well as attachment of the anchoring compound to the indicator may be accomplished using carboxylic, amino, aldehyde, bromoacetyl, iodoacetyl, thiol, epoxy or other reactive functional groups, as well as residual free radicals and radical cations, through which a binding reaction may be accomplished and according to any suitable methods, e.g., thermal processes, photo-initiated processes, catalyzed reactions, and the like. For example, a chromatographic medium may be amine-functionalized through contact with an amine-containing compound, such as 3-aminopropyltriethoxy silane, to increase the amine functionality of the surface and bind the anchoring compound to the surface via, e.g., aldehyde functionality of the anchoring compound. A surface functional group may also be incorporated on a particle-type anchoring compound as a reactive functionality, for instance when the surface of the particle contains a relatively high surface concentration of polar groups. In certain cases, the particle may be capable of direct bonding to a chromatographic medium and/or an indicator without the need for further modification.

It should be understood that, besides covalent bonding, other attachment techniques, such as charge-charge interactions, may also be utilized for attaching the anchoring compound to the chromatographic medium and/or for attaching the indicator to the anchoring compound. For instance, a charged anchoring compound, such as a positively charged polyelectrolyte anchoring compound, may be immobilized on a negatively charged chromatographic medium, such as negatively charged porous nitrocellulose membrane, through charge-charge interactions between the two. Similarly, a negatively charged indicator, such as a diazonium ion, may be immobilized on a positively charged anchoring compound.

In addition, it should be understood that the disclosure is not limited to attachment of a single indicator to an anchoring compound. For instance, when utilizing a multifunctional anchoring compound, indicator density at a detection zone may be increased through binding of a plurality of indicators to a single anchoring compound molecule. For example, a multifunctional dendrimeric anchoring compound such as 64-cascade: 1,4-diaminobutane[4]:1-azabutylidene)60-propylamine (available as Astramol(Am)64 dendrimer from DSM) can bind a plurality of indicators (e.g., N-(1-naphthyl) ethylenediamine dihydrochloride) in any suitable process as is generally known in the art. According to one method, for example, the indicator may be functionalized with a reactive moiety that may be used to bond a plurality of the indicators to an anchoring compound while protecting the indicator moiety of the small molecule indicator. For instance, a solution can be formed including about 11 mg N-(1 -naphthyl) ethylenediamine dihydrochloride indicator and a suitable solvent (e.g., DMSO) including any additional reagents to facilitate bonding (e.g., about 18 mg sodium dicarbonate). The indicator may then be functionalized in solution with a reactive moiety for bonding to the anchoring compound. For example, about 9 mg N-hydroxysuccinimidyl-4-azidosalicylic acid (NHS-ASA, available from Pierce Biotech.) may be added to the solution and upon shaking (under dark) may functionalize the indicator with the photoreactive moiety. Upon addition of the dendrimeric anchoring compound and establishment of suitable reaction conditions (e.g., irradiation using a UV lamp for about 20 minutes at 365 nm), the anchoring compound can bind a plurality of the indicators. The solution containing the anchoring compound/indicator complex thus formed may then be further treated as desired and applied to a chromatographic medium. For instance, the solution thus formed may be dialyzed in acidic water using a membrane (e.g., a 3,500 cut-off membrane from Pierce Biotech). The dialyzed solution may then be applied to a chromatographic medium (e.g., a nitrocellulose membrane) and crosslinked to form a detection zone, for instance a detection zone for nitrite.

Once applied, crosslink reactions may occur to form the crosslinked network. Depending upon the nature of the materials of any specific embodiment, crosslink reactions may occur between two of the chromatographic medium surface, the anchoring compound, and the indicator as well as between any two of the same components as inter-crosslinks (e.g., between two anchoring compounds or between two small molecule indicators) or among a single component as intra-crosslinks (e.g., between two functional moieties on a single polymeric anchoring compound). For example, a multi-functional anchoring compound may crosslink the indicator, may crosslink adjacent anchoring compounds (inter-crosslinking), and/or may crosslink within itself (intra-crosslinking). Similarly, multi-functional indicators may crosslink with each other and/or with adjacent anchoring compounds to form crosslinks within the crosslinked indicator network. For example, a multi-functional anchoring compound and an indicator may be applied as a mixture to the detection zone, optionally with a suitable crosslinking agent and/or a crosslink initiator. Upon initiation of the binding reactions (e.g. photoinitiation), a crosslinked network may be formed that includes the securely immobilized indicator.

Any suitable binding mechanism may be employed to facilitate crosslinking. By way of illustration only, examples of anchoring compounds that may be cured via a photoinitiated crosslinking process may include those including unsaturated monomeric or oligomeric groups such as, without limitation, ethylene, propylene, vinyl chloride, isobutylene, styrene, isoprene, acrylonitrile, acrylic acid, methacrylic acid, ethyl acrylate, methyl methacrylate, vinyl acrylate, allyl methacrylate, tripropylene glycol diacrylate, trimethylol propane ethoxylate acrylate, epoxy acrylates, such as the reaction product of a bisphenol A epoxide with acrylic acid; polyether acrylates, such as the reaction product of acrylic acid with an adipic acid/hexanediol-based polyether, urethane acrylates, such as the reaction product of hydroxypropyl acrylate with diphenylmethane-4,4'-diisocyanate, and polybutadiene diacrylate oligomer.

In one embodiment, the anchoring compound may include a polycarboxylic acid or cyclic anhydride groups, either of which may form ester bonds in the presence of suitable pH and temperature conditions between both a reactive moiety of a small molecule indicator (e.g., a cyclodextrin moiety) and a polysaccharide chromatographic medium (e.g., a cellulose). The anchoring compound may also be a biological macromolecule, such as a protein or a polynucleic acid. Proteins, such as antibodies and albumin, are known to be capable of being immobilized on chromatographic mediums such as nitrocellulose. Indicators may be attached covalently to such biological anchoring compounds via existing or altered chemistries. For instance, the indicator may be bound to an albumin anchoring compound via the lysine groups or carboxylic groups of the protein. Such attachment chemistry is well known in the art. Similarly, methods of covalently binding a base such as may be present in a polynucleotide anchoring compound with a small molecule indicator including functional reactivity are generally known in the art. The anchoring compound may then be crosslinked with inter- and intra-crosslinks to form the crosslinked network containing the indicator.

The indicator moiety of the small molecule indicator may be protected during the network formation processes. For instance, the anchoring compound and/or the chromatographic medium may include reactive functionality that does not react with the indicator moiety during formation. Optionally, the other system components may include reactive functionality that preferentially reacts under the network formation conditions with a moiety of the small molecule indicator other than the indicator itself. Accordingly, reaction conditions may then be controlled so as to preferentially form the desired bonds while protecting the indicator moiety. In another embodiment, the small molecule indicator may include a plurality of similar reactive sites, for instance in the case of a polyamine diazonium compound the small molecule indicator may include a plurality of reactive amines that may be utilized to bind the small molecule indicator to an anchoring compound. Upon reaction of the anchoring compound with the indicator, a portion of the amine groups may be used to bind the indicator to the anchoring compound and optionally in cross-linking the network, and the reactivity of the indicator may be maintained.

Various embodiments of forming an assay device that may be used to facilitate detection of an analyte will now be described in more detail. Referring to FIG. 1, for instance, one embodiment of a membrane-based flow-through assay device 20 is illustrated. As shown, the device 20 contains a chromatographic medium 23 optionally supported by a rigid material 21. The chromatographic medium 23 may be formed from any of a variety of materials through which the test sample is capable of passing. For example, the materials used to form the medium may include, but are not limited to, natural, synthetic, or naturally occurring materials that are synthetically modified, such as polysaccharides (e.g., cellulose materials such as paper and cellulose derivatives, such as cellulose acetate and nitrocellulose); silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the chromatographic medium is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The chromatographic medium 23 defines a detection zone 31 within which is contained a crosslinked network containing the indicator (not shown). The crosslinked network is affixed to the surface of the chromatographic medium 23 so that it does not diffuse through the matrix of the chromatographic medium 23. The detection zone 31 may generally provide any number of distinct detection regions so that, in one embodiment, a user may determine the concentration of a particular analyte within a test sample. Each region may include a crosslinked network that may contain the same indicator or may contain different indicators for capturing multiple analytes. For example, the detection zone 31 may include two or more distinct detection regions (e.g., lines, dots, etc.). The detection regions may be disposed as discrete layers that may be in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device.

The device 20 may also contain an absorbent pad 28. The absorbent pad 28 generally receives fluid that has migrated through the entire chromatographic medium 23. As is well known in the art, the absorbent pad 28 may assist in promoting capillary action and fluid flow through the membrane 23. To initiate the detection of an analyte within the test sample, a user may directly apply the test sample to an application pad 24 of the chromatographic medium 23 that is in fluid communication with the chromatographic medium 23. Some suitable materials that may be used to form the application pad 24 include, but are not limited to, nitrocellulose, cellulose, porous polyethylene pads, and glass fiber filter paper. If desired, the application pad 24 may also contain one or more assay pretreatment reagents, either diffusively or non-diffusively attached thereto.

In the illustrated embodiment, the test sample travels from the application pad 24 to a conjugate pad 22 that is placed in communication with one end of the application pad 24. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used.

To facilitate detection of the presence or absence of an analyte within the test sample, various reagents may be immobilized at the conjugate pad 22. For example, a test sample including an analyte such as glucose may travel to the conjugate pad 22, where the analyte mixes with reagents including glucose oxidase, peroxidase, and a suitable buffer. Upon mixture of the sample with the reagents, the glucose oxidase catalyzes the oxidation of glucose, yielding the peroxidase hydrogen peroxide. Because the conjugate pad 22 is in fluid communication with the chromatographic medium 23, the materials may migrate from the conjugate pad 22 to a detection zone 31 within which is a crosslinked network that includes an indicator, such as a benzidine-type indicator (e.g., TMB). In the presence of the peroxidase, the hydrogen peroxide causes a color change in the indicator. Obviously, the specific location of any or all of the reagents may be optimized with respect to the location of the detection zone. For instance, in some embodiments, it may be preferred to include a buffer diffusively immobilized within the detection zone 31.

For the embodiment shown in FIG. 1, as analyte concentration increases in a test sample, more analyte (or a reaction product thereof) may react with the indicator within the detection zone 31. The increased quantity of reaction at the detection zone 31 results in an increase in signal intensity. From this increase in signal intensity, the presence or concentration of the analyte may be readily determined. For example, in one embodiment, the amount of analyte is directly proportional to the signal intensity at the detection zone 31, $I_1$. If desired, the signal intensity $I_1$ may be plotted versus the analyte concentration for a range of known concentrations to generate an intensity curve. To determine the quantity of analyte in an unknown test sample, the signal intensity may then be converted to analyte concentration according to the intensity curve.

It should be understood that one or more distinct regions of the detection zone 31 may exhibit the above-described relationship between signal intensity and analyte concentration; however, each and every distinct region need not exhibit such a relationship. For example, in some embodiments, only one of multiple distinct regions may exhibit a signal intensity that is directly proportional to the concentration of the analyte. The signal intensity of other distinct regions, such as those used to reduce false positives, may otherwise remain constant, or exhibit an increase and/or decrease in signal intensity. So long as at least one distinct region of the detection zone 31 satisfies the direct relationship, the signal intensity exhibited by the detection zone 31 is considered directly proportional to the enzyme concentration.

Referring to FIG. 1, the assay device 20 may also include a control zone 32. Control zone 32 may be utilized to determine if the device is working properly. Control zone 32 may be provided with a receptive material that is capable of binding to reagents that may be diffusively dispersed on the chromatographic medium 23 upstream of the control zone 32. More specifically, detectable reagents may be employed that flow through the chromatographic medium 23 upon contact with a sufficient volume of the test sample. These detectable reagents may then be observed, either visually or with an instrument, within the control zone 32. The control reagents generally contain a detectable substance, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If desired, the detectable substances may be disposed on particles such as those described above.

The location of the control zone 32 may vary based on the nature of the test being performed. In the illustrated embodiment, for example, the control zone 32 is defined by the chromatographic medium 23 and positioned downstream from the detection zone 31. The control zone 32 may contain a material that is non-diffusively immobilized and forms a chemical and/or physical bond with the detectable reagents. For example, in some embodiments, the binders may contain a biological receptive material. For example, the receptive material may be a biological receptive material. Such biological receptive materials are well known in the art and may include, but are not limited to, antigens, haptens, antibodies, protein A or G, avidin, streptavidin, secondary antibodies, and complexes thereof. In some cases, it is desired that these biological receptive materials are capable of binding to a specific binding member (e.g., antibody) present on the detectable reagents. Alternatively, various non-biological materials may be utilized for the detectable reagent receptive material. For instance, in some embodiments, the receptive material may include a polyelectrolyte that may bind to the detectable reagents. Various polyelectrolytic binding systems are described, for instance, in U.S. Patent App. Publication No. 2003/0124739 to Song, et al., which is incorporated herein in it entirety by reference thereto for all purposes. In alternative embodiments, however, the control zone 32 may simply be defined by a region of the absorbent material 28 to which the detectable reagents flow after traversing through the chromatographic medium 23.

Regardless of the particular technique selected, the application of a sufficient volume of the test sample to the device 20 will cause a signal to form within the control zone 32, whether or not the analyte is present. Among the benefits provided by such a control zone is that the user is informed that a sufficient volume of test sample has been added without requiring careful measurement or calculation. This provides the ability to use the lateral flow device 20 without the need for externally controlling the reaction time, test sample volume, etc.

One benefit of the disclosed lateral flow device is its ability to readily incorporate one or more additional zones to facilitate analyte detection. For example, referring again to FIG. 1, one such zone is a quenching zone 35. The quenching zone 35 is configured to remove compounds from the test sample that would otherwise interfere with the accuracy of the detection system. For example, contaminants within the test sample (e.g., phenolics, bilirubin, urobilinogen, etc.) may react with the indicator within the detection zone 31 and form a detectable compound, thereby producing a "false negative" result. Thus, the quenching zone 35 may contain a quenching agent, such as a diazonium ion, that is capable of reacting with the reaction contaminants. The quenching agent may be the same or different than the indicator used within the detection zone 31. The quenching agent may non-diffusively immobilized within the quenching zone 35 in the manner described above so that it does not flow through the medium 23 and interfere with testing. The location of the quenching zone 35 may vary, but is typically positioned upstream from the detection zone 31 and the location at which the sample is applied to avoid interference with detection. For example, in the illustrated embodiment, the quenching zone 35 is positioned between the sample application zone 24 and the conjugate pad 22.

In addition to the zones specified above, the lateral flow device 20 may also include other optional zones. For example, in one embodiment, the lateral flow device 20 may include an accelerator zone (not shown) in which is contained an accelerator for an enzyme-catalyzed substrate reaction. Typically, the accelerator is diffusively immobilized within the accelerator zone in the manner described above so that it may flow through the medium 23 upon contact with the test sample. The location of the accelerator zone may generally vary, so long as it positioned upstream from the detection zone 31. For example, in some embodiments, the accelerator zone may be positioned at a location (e.g., sample application zone 24) that is upstream from the conjugate pad 22. Due to the separation provided between the substrate provided in the conjugate pad 22 and accelerator, the likelihood of any premature reaction therebetween is thus reduced. It should be understood, however, that the accelerator may nevertheless be combined with a substrate in some applications.

While the disclosed subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A lateral flow assay device for detecting the presence or quantity of an analyte in a test sample comprising a chromatographic medium that includes a conjugate pad located upstream of a detection zone, wherein a crosslinked network is non-diffusively immobilized within the detection zone, the crosslinked network containing a plurality of small molecule indicators that are configured to undergo a detectable color change in the presence of the analyte, the small molecule indicators of the crosslinked network being crosslinked to one another either directly or via a crosslinking agent that binds the small molecule indicators, the crosslinked network further comprising an anchoring compound that links the chromatographic medium and one of the plurality of small molecular indicators of the crosslinked network.

2. The lateral flow assay device of claim 1, wherein the small molecule indicator is covalently bound to the anchoring compound.

3. The lateral flow assay device of claim 1, wherein the small molecule indicator is bound to the anchoring compound via charge-charge interactions.

4. The lateral flow assay device of claim 1, wherein the anchoring compound is covalently bound to the chromatographic medium.

5. The lateral flow assay device of claim 1, wherein the anchoring compound is bound to the chromatographic medium via charge-charge interactions.

6. The lateral flow assay device of claim 1, wherein the anchoring compound is a macromolecular compound.

7. The lateral flow assay device of claim 6, wherein the macromolecular anchoring compound is a polymer.

8. The lateral flow assay device of claim 1, wherein the small molecule indicators include a diazonium compound.

9. The lateral flow assay device of claim 1, wherein the small molecule indicators include a benzidine compound, phthalein compound, aminobenzaldehyde compound, or a combination thereof.

10. The lateral flow assay device of claim 1, further comprising an enzyme substrate contained within the conjugate pad.

11. The lateral flow assay device of claim 1, further comprising a control zone.

12. The lateral flow assay device of claim 1, further comprising detectable reagents in fluid communication with the chromatographic medium.

13. The lateral flow assay device of claim 1, wherein the crosslinked network is formed with electromagnetic radiation.

14. The lateral flow assay device of claim 13, wherein the radiation is ultraviolet radiation.

15. The lateral flow assay device of claim 1, wherein the crosslinked network is formed with thermal energy.

\* \* \* \* \*